United States Patent [19]

Lajoie

[11] Patent Number: 5,346,704
[45] Date of Patent: Sep. 13, 1994

[54] POLYFUNCTIONAL AGROCHEMICAL BICARBONATE-CONTAINING COMPOSITIONS

[75] Inventor: M. Stephen Lajoie, Basking Ridge, N.J.

[73] Assignee: Church & Dwight Co., Inc., Princeton, N.J.

[21] Appl. No.: 104,561

[22] Filed: Aug. 11, 1993

Related U.S. Application Data

[62] Division of Ser. No. 907,625, Jul. 2, 1992.

[51] Int. Cl.$^5$ .................... A01N 59/00; A01N 25/12; A01N 25/24; A01N 25/32
[52] U.S. Cl. ................................ 424/717; 424/407; 424/408; 424/409; 424/417; 424/489; 424/715; 424/716; 514/388; 71/DIG. 1; 504/121
[58] Field of Search .............. 424/405, 406, 407, 408, 424/409, 421, 489, 715, 716, 717; 71/64.07, DIG. 1; 504/121; 514/388

[56] References Cited

U.S. PATENT DOCUMENTS

| 536,155 | 5/1894 | Noyes | 424/466 |
|---|---|---|---|
| 1,560,558 | 11/1925 | Fulton et al. | 424/715 |
| 3,541,213 | 11/1970 | Klopping | 514/388 |
| 4,599,233 | 7/1986 | Misato et al. | 424/717 |
| 5,123,950 | 6/1992 | Homma et al. | 71/11 |
| 5,217,719 | 6/1993 | Yorozu et al. | 424/466 |

FOREIGN PATENT DOCUMENTS

| 52-7438 | 1/1977 | Japan . |
| 53-96319 | 8/1978 | Japan . |
| 58-97363 | 6/1983 | Japan . |

*Primary Examiner*—Richard L. Raymond
*Assistant Examiner*—John D. Pak
*Attorney, Agent, or Firm*—Charles B. Barris

[57] ABSTRACT

This invention provides a dry pulverulent composition which is comprised of (1) a particulated agrochemical ingredient such as a herbicide; and (2) an inorganic salt ingredient such as sodium, potassium or ammonium bicarbonate or a mixture thereof, which is adsorbed on the surface of the agrochemical particles. The agrochemical ingredient can be a mixture of two or more biologically active organic compounds. The adsorbed inorganic salt ingredient also can be in a blend with a water-soluble or water-dispersible organic polymer ingredient as a film coating, and the coating of ingredients can function as a slow-release medium in the presence of moisture.

5 Claims, No Drawings

POLYFUNCTIONAL AGROCHEMICAL BICARBONATE-CONTAINING COMPOSITIONS

This application is a division, of application Ser. No. 07/907,625, filed Jul. 2, 1992.

CROSS-REFERENCE TO RELATED APPLICATION

The subject matter of the present patent application is related to that disclosed in patent application Ser. No. 07/881,696 (Docket D14792), filed May 12, 1992, now abandoned.

BACKGROUND OF THE INVENTION

Fine chemical sales for agricultural purposes in the United States totalled about 13 billion dollars in 1990. The United States market for organic pesticide intermediates is about 986 million dollars per year, which include chemicals such as nitrites, amines, carboxylic acids, anilines, organophosphorus compounds, mercaptans, phenols, benzenes, alkane/alkenes, pyridines, alcohols and aldehydes.

Agricultural pesticide sales at the producer level in the United States in 1991 were about 7.6 billion dollars. Pesticide sales represent an important segment of the agrochemical industry in the United States and in other world markets, mainly for fungicide, herbicide and insecticide applications.

The control of phytopathogenic fungi is of great economic importance since fungal growth on plants or on parts of plants inhibits production of foliage, fruit or seed, and the overall quality of a cultivated crop.

There is also a serious worldwide problem of mold growth in food materials, such as grains, animal feeds, animal feed ingredients, and hay. This problem is most serious in tropical zones of both the eastern and western hemispheres, where sustained high humidities cause excessive moisture to be absorbed in such products.

Because of the vast economic ramifications of fungal propagation in agricultural and horticultural cultivations, a broad spectrum of fungicidal and fungistatic products have been developed for general and specific applications.

With respect to herbicide developments, weed control is essential in the cultivation of important agricultural crops such as corn, peanuts and cotton, and in the cultivation of many horticultural species. Also, the presence of weeds on non-cropped areas can be a fire hazard, or can result in undesirable drifting of sand or snow, or can cause discomfort to persons with allergies. Control of weeds is particularly beneficial when it permits the selective control of such plants without concurrent injury to desirable crops or vegetation.

Chemical herbicides are classified according to the type of activity they possess. A given compound may have more than one type of activity depending upon its mode of application and the rate at which it is applied. In addition, herbicides are usually classified as selective or non-selective pre-emergents or post-emergents.

The most effective pre-emergence herbicide is one which is selective in its nature. If the designated compound can kill the seed and germinated seedlings of undesirable plants without harm to the seed and germinated seedlings of the crop, there will not be any problem of overpenetration of the soil by the herbicide.

Post-emergence herbicides are applied after the crop and weeds have attained substantial height. In general, if a compound is found to have post-emergence activity it will not be selective.

Some herbicides are effective through contact, and others are taken up from the soil by root systems. Herbicide types include defoliants, desiccants, eradicants, systemics and selective herbicides, and related plant growth regulators.

With respect to insecticide developments, a wide variety of ornamental and agricultural plants are susceptible to infestation by insects and arachnids. The pests inflict damage by consuming foliage and roots, withdrawing juices from the plants, secreting toxins, and infecting with diseases.

Field crops which require protection from pests include such valuable crops as soybeans, corn, peanuts, cotton, alfalfa and tobacco. In addition, vegetables such as tomatoes, potatoes, sugar-beets, carrots, and the like, and nuts, ornamentals, apples, peaches, peas, citrus fruit and grape also require protection from the ravages of such pests.

Insects which are difficult to control include those which inhabit the soil and cause destruction of the root systems of valuable agricultural crops. Corn rootworms are the larvae of several beetle species of the genus Diabrotica. The adult beetles lay their eggs in the soil of a maturing corn crop. The eggs lay dormant in the soil until the following spring, then they hatch in response to favorable soil temperatures and the larvae feed on the roots of young corn plants causing reduction in yield.

A broad scope of insecticide compounds have been developed to combat insects which are harmful to agricultural and horticultural plants. Illustrative of insecticide compositions are those described in U.S. Pat. Nos. 3,217,037; 3,506,698; 3,576,834; 3,636,111; 3,755,364; 3,875,232; 4,028,413; 4,128,581; 4,415,743; 4,640,927; 4,804,653; 4,839,349; 5,010,068; 5,087,456; 5,087,456; 5,096,928; and references cited therein.

Of particular interest with respect to the present invention embodiments are pesticide compositions which contain one or more inorganic bicarbonate or carbonate compounds. It is known that bicarbonate and carbonate compounds exhibit biocidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillum italicum* and *Penicillum digitalum*.

Japanese patent 56043207 describes a biocidal composition containing sodium bicarbonate and a polyglycerol fatty acid ester. The biocide controls *Penicillum digitatum* on oranges, *Sphaerotheca fuligenea* on cucumbers, *Piricularia oryzae* on rice, and mosaic virus on tomatoes.

Japanese patent 57062208 describes horticultural fungicides in which the addition of sodium bicarbonate to polyoxin or thiophanatemethyl increases the fungicidal activity of the organic biocide against botrytis cinerea on cucumbers.

There remains a continuing need for the development of new and more effective agrochemical compositions which possess preventive, curative and systemic biological activity for the protection of cultivated plants, with a minimum of undesirable phytotoxic side effects.

Accordingly, it is an object of this invention to provide an agricultural composition which is a combination of inorganic and organic compounds exhibiting pesticidal properties.

It is another object of this invention to provide a dry particulate composition which is a combination of ingredients which include a bicarbonate-containing inorganic ingredient which enhances the biocidal activity of a pesticide ingredient.

Other objects and advantages of the present invention shall become apparent from the accompanying description and examples.

DESCRIPTION OF THE INVENTION

One or more objects of the present invention are accomplished by the provision of a dry pulverulent composition which has a combination of ingredients comprising (1) a particulated agrochemical ingredient; and (2) an inorganic salt ingredient selected from alkali metal and ammonium bicarbonates, which is adsorbed on the surface of the agrochemical ingredient.

The agrochemical particles can be in the form of a fine dusting powder with an average particle diameter less than about 0.5 micron, and can range up to granular size particles for compositions which are being utilized for applications such as soil treatment.

A typical dry pulverulent composition has an average particle size diameter in the range between about 10–600 microns.

The agrochemical ingredient can consist of one or more biologically active organic compounds. Biologically active organic compounds are illustrated by fungicides, herbicides, insecticides, plant growth regulators, fertilizers, and the like.

An agrochemical fungicide ingredient can be selected from a wide variety of organic compounds or mixtures which are known and used in agriculture and horticulture applications, such as those listed in Agricultural Chemicals, Book IV, Fungicides, 1989 Revision (W. T. Thomson, Thomson Publications, Fresno, Calif. 93791).

The general categories of fungicidal-active compounds include anilides, dithiocarbamates, halogenated derivatives, heterocyclic nitrogen derivatives, organometallic derivatives, and the like.

Illustrative of fungicidal compounds are carbendazim, benomyl, thiophanate-methyl, thiabendazole, fuberidazole, dichlofluanid, cymoxanil, oxadixyl, metalaxyl, furalaxyl, benalaxyl, fenarimol, iprodione, procymidone, vinclozolin, penconazole, myclobutanil, pyrazophos, ethirimol, ditalimfos, tridermorph, triforine, nuarimol, triazbutyl, guazatine, propiconazole, prochloraz, flutriafol, chlortriafol, triadimefon, triadimenol, dichlobutrazol, fenpropimorph, fenpropidin, chlorozolinate, fenfuram, carboxin, oxycarboxin, methfuroxam, dodemorph, blasticidin S, kasugamycin, edifenphos, kitazin P, cycloheximide, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarbamate, techlofthalam, bupirimate, etaconazole, cypofuram, biloxazol,-dimethirimol, fenapanil, pyroxyfur, polyram, maneb, mancozeb, captafol, chlorothalonil, anilazine, thiram, captan, folpet, zineb, propineb, binapactryl, nitrothalisopropyl, dodine, dithianon, fentin hydroxide, fentin acetate, tecnazene, quintozene, dichloran, and the like.

An agrochemical herbicide ingredient can be selected from a wide variety of organic chemical structures known and used in pest control applications.

Amide herbicides are exemplified by commercial products such as Lasso and Dual, which are effective for pre-emergent or pre-planting applications.

Arsenical herbicides include cacodylic acid and the salts of monomethylarsinic acid and dimethylarsinic acid. Cacodylic acid is a defoliating or desiccating contact herbicide. Arsinic acid salts have lower contact toxicity and act through absorption.

Carbamate and thiocarbamate herbicides include Belanal, Betanex, Sutan, Eptam, and similar trademark products. These herbicides usually are applied to the soil and are taken up through the root systems.

Carboxylic acid herbicides are illustrated by commercial products such as Banvel, Garlon and 2,4-D. Various of these herbicides can be applied to the soil or to foliage, and are effective against broad leaf weeds.

Dinitroaniline herbicides include Balan and Treflan commercial products, which are applied to the soil to inhibit root growth and shoot growth, and exhibit low translocation.

Heterocyclic nitrogen-containing herbicides are illustrated by Aatrex, Basagran, Sencor and Velpar, which are applied to the soil for pre-emergent control.

Organophosphate compounds are useful as plant growth regulators and herbicides. This type of organic biocide structure is illustrated by Bensulide and Betasan.

Urea herbicides are nonselective and usually are soil applied. Urea-type commercial products include Lorox and Tupersan.

Quaternary herbicides include commercial products such as Avenge, Diquat and Paraquat, which have utility as contact foliars.

Other commercially available herbicides include Atrazine, Bentazon, Bromacil, Casoron, Chloroamben, Delapon, Diuron, Fluometuron, Glphosate, Linuron, Picloram, Trifluralin, and the like.

The types of weeds which are controlled by herbicide agrochemicals include barnyard grass, green foxtail, wild oats, nightshade, velvetleaf, annual morningglory, yellow nutsedge, pigweed, downy brome, and the like.

An agrochemical insecticide ingredient can be selected from a wide variety of organic chemical structures, such as those listed in Agricultural Chemicals, Book I, Insecticides, 1989 Revision (W. T. Thomson, Thomson Publications, Fresno, Calif. 93791).

The general categories of insecticidal-active organic compounds include chlorinated hydrocarbon derivatives, phosphorated derivatives, pyrethroids, acylureas, and the like.

The chlorinated hydrocarbon insecticides usually act as stomach and contact poisons affecting the nervous system. They are persistent in the environment and tend to accumulate in animal fatty tissue, as exemplified by DDT and chlordane.

The organic phosphates generally are contact and/or stomach poisons. They are less persistent in the environment than the chlorinated hydrocarbons. They are toxic since they generally are cholinesterase inhibitors, which interfere with nerve impulse transmission. Most of these compounds are characterized by relatively low $LD_{50}$ values, although the value for malathion is 1400. Parathion is one of the best known organic phosphate systemic insecticides, and is considered a dangerous material to handle.

The carbamates are similar in action to the organic phosphate insecticides. These insecticides usually are not magnified in the food chain, and are characterized by rapid breakdown.

The synthetic pyrethroids react well with synergists and exhibit relatively low mammalian toxicity. Generally they break down rapidly and leave little residue.

Illustrative of other insecticidal compounds are chlorfluazuron, chlorpyrifos, chlorpyrifos methyl, bromophos, diazinon, malathion, trichlorfon, dimethoate, phorate, lindane, toxaphene, diflubenuron, methomyl, propoxur, carbaryl, cyhexatin, cypermethrin, permethrin, fenvalerate, dicofol, tetradifon, propargite, and the like.

An agrochemical plant growth regulator ingredient can be selected from the types of organic chemical structures which are known to exhibit phytohormone activity, such as 3-indolealkanoic acids, deterpenoid acids, cytokinins, chlorosubstituted phenoxyacetic acids, naphthaleneacetic acids, and the like.

An invention plant growth regulating composition preferably has a content of an organic plant growth stimulant ingredient such as a surfactant.

Plant growth regulator compounds include abscisic acid, gibberellic acid, 3-indoleacetic acid, 2,4-dichlorophenoxyacetic acid, 2-naphthylacetic acid, 2,3,5-triiodobenzoic acid, phenyl indole-3-thiolobutyrate, kinetin, zeatin, 6-benzylaminopurine, and the like.

An agrochemical fertilizer ingredient can be selected from nitrogen-containing and phosphoruscontaining organic compounds such as urea, melamine, hexamine, benzoquanamine, dicyanodiamide, ammeline, cyanuric acid, melamine nitrate, triethyl phosphite, and the like.

The inorganic salt ingredient is selected from compounds which include sodium bicarbonate, potassium bicarbonate, lithium bicarbonate and ammonium bicarbonate. In a further embodiment, the inorganic salt ingredient can include an additional compound selected from sodium carbonate, potassium carbonate, lithium carbonate and ammonium carbonate.

Illustrative of inorganic salt ingredients in a formulation are sodium, potassium, lithium or ammonium bicarbonate; or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt compound normally is determined by pH control considerations when aqueous formulations are prepared. The content of a carbonate salt compound can be varied to control the pH at a desired level in the range of 7.5–12. Pesticidal formulations of the present invention tend to have a higher biocidal activity at higher pH values.

The present invention also contemplates a pulverulent formulation which is a dry blend of at least two compositions as defined above.

In an invention pulverulent composition, the inorganic salt ingredient is adsorbed on the surface of the agrochemical particles. The adsorbed phase will be in the form of solid microspecks. The content of adsorbed inorganic salt ingredient normally will vary in the range between about 1–80 weight percent, based on the weight of agrochemical ingredient.

In another embodiment this invention provides a dry pulverulent composition which has a combination of ingredients comprising (1) a particulated agrochemical ingredient; (2) an inorganic salt ingredient selected from alkali metal and ammonium bicarbonates, which is adsorbed on the surface of the agrochemical ingredient; and (3) a surfactant ingredient.

The surfactant ingredient is a cationic, anionic or nonionic organic compound or a mixture thereof, and the content of the surfactant can be in the range between about 1–20 weight percent, based on the weight of water-insoluble ingredients.

Suitable surfactants include cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; and the like.

In another embodiment this invention provides a dry pulverulent composition which has a combination of ingredients comprising (1) a particulated agrochemical ingredient; (2) an inorganic salt ingredient selected from alkali metal and ammonium bicarbonates, which is adsorbed on the surface of the agrochemical ingredient; and (3) a compatibility enhancing ingredient selected from water-soluble organic compounds which are in solid form at a temperature below about 10° C., and which have a low vapor pressure at ambient temperatures.

The content of compatibility enhancing ingredient can be in the range between about 0.5–20 weight percent, based on the weight of ingredients.

The term "water-soluble" as employed herein refers to an organic compound which has a solubility of at least about one gram per 100 grams of water at 25° C.

Suitable compatibility enhancing organic compounds include acetamide, acetylurea, alanine, aminoquanidine, aminopyridine, arabinose, citrate salt, cyclohexanol, dihydroxyacetone, dihydroxybenzene, dimethylurea ethanolamine, ethyl alaninate, ethylglycine, ethylurea, ethylenedisulfonate salt, ethyleneurea, paraformaldehyde, fucose, glutamate salt, glycerol, glycerol nitrate, glycerol phosphate salt, glycogen, glycolic aidehyde, glyoxal, guanidine, hexamine, mannitol, fructose, glucose, hydroxyurea, lactate salt, lactose, lysine, maleic amide, malonate salt, maltose, maltodextrin, methoxypyridine, methyl acetate, methyl carbamate, methyl ethyl sulfone, methyl glucoside, methylhydantoin, methylinositol, methylthiourea, methyluracil, methylurea, muconate salt, nitropentanediol, nitrourethane, pentaglycerol, phenylenediamine, polydextrose, propionamide, propyl carbamate, propylurea, purine, ribose, semicarbazide, sorbate salt, succinimide, sucrose, tartarate salt, tetrahydrobenzoate salt, tetrahydroquinoline, thiourea, threonine, triaminobenzene, triethylphosphine oxide, triethylenetetramine, urea, xylose, xylylene glycol, and the like.

In another embodiment this invention provides a dry pulverulent composition which has a combination of ingredients comprising (1) a particulated agrochemical ingredient; (2) an inorganic salt ingredient selected from alkali metal and ammonium bicarbonates, which is adsorbed on the surface of the agrochemical ingredient; and (3) a particulated inert diluent.

The inert diluent is a water-insoluble inorganic carrier, which can be incorporated in a quantity between about 0.1–5 parts per part of the composition ingredients.

Illustrative of inert diluents are bentonite, calcium carbonate, magnesia, gypsum, kieselguhr, diatomaceous earth, zeolites, and the like. Granules or larger particles can be formed by pelleting an invention pulverulent composition in admixture with a powdered inert diluent.

In another embodiment this invention provides a slow-release pulverulent composition which has a combination of ingredients comprising (1) a particulated agrochemical ingredient; (2) a blend ingredient comprising (a) an inorganic salt selected from alkali metal and ammonium bicarbonates, and (b) a water-soluble or water-dispersible organic polymer, wherein the blend ingredient is adsorbed on the surface of the agrochemical particles, and the blend ingredient functions as a slow-release medium in the presence of moisture.

The organic polymer in the blend ingredient typically will be present in a quantity between about 1–10 parts by weight per part of inorganic salt compound.

The rate of inorganic salt compound release from the agrochemical particle surface under moisture conditions can be controlled by the quantity and type of organic polymer component in the blend ingredient.

Low molecular weight hydrophilic polymers will release the inorganic salt at a relatively fast rate. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release inorganic salt at a relatively fast rate. Polyethylene oxide (M.W. of 4,000,000) or partially hydrolyzed polyvinyl acetate will release at a relatively slow rate. Polyvinylpyrrolidone will release inorganic salt at an immediate rate.

Gradual removal of the blend ingredient from the surface of the agrochemical particles frees the agrochemical to exhibit enhanced biological activity in plant treatment applications.

In a further embodiment this invention provides a process for preparing a dry pulverulent composition which comprises (1) forming an aqueous solution of an inorganic salt ingredient selected from alkali metal and ammonium bicarbonates; (2) admixing the solution with a particulated water-insoluble agrochemical ingredient to form a two-phase suspension medium; and (3) removing the water from the suspension medium to provide agrochemical ingredient having inorganic salt ingredient adsorbed on the surface of the agrochemical particles.

The admixing of the step (1) aqueous solution and the agrochemical ingredient can be accomplished at room temperature with appropriate stirring. The step (1) aqueous solution additionally can contain a water-soluble or water-dispersible organic polymer ingredient.

The aqueous phase can be removed by conventional means such as vacuum distillation.

Another effective means for preparing an invention dry pulverulent composition is by the application of electrostatic coating conditions. Electrostatic equipment and particle coating procedures are described in technical publications such as U.S. Pat. Nos. 3,868,336; 4,380,320; 4,780,331; 5,000,978; and references cited therein.

In this type of process, a finely divided inorganic salt powder ingredient is uniformly distributed on the surface of agrochemical particles by means of an electrostatic powder charging and delivery system.

Optionally, an anti-caking or free-flow aid can be included as an additive in the final form of an invention pulverulent composition. Useful additives include mannitol, sorbitol, phosphorus pentoxide, calcium sulfate, barium oxide, calcium chloride, and the like.

As described hereinabove, an invention dry pulverulent composition can be in the form of dusting powders, granules or pellets, and can be utilized as such for pest control or plant growth regulation or fertilization applications.

An invention dry pulverulent composition also can function as a dispersible powder when it contains a surfactant ingredient which facilitates dispersion of the powder in an aqueous medium.

A present invention dry pulverulent composition has a unique combination of properties, and provides versatility and advantage in a broad range of agricultural and horticultural applications.

Each of the bicarbonate and carbonate components either singly or together in the inorganic salt ingredient exhibits fungicidal activity when an invention composition is applied in solid form or as an aqueous medium in agricultural pest control applications.

The physical combination of the inorganic salt ingredient adsorbed on the agrochemical particles prevents any settling or inhomogeneous separation of the ingredients in a dry pulverulent composition.

The adsorbed state of the inorganic ingredient contributes stability to the agrochemical ingredient under variable conditions of temperature and atmosphere during storage.

The molecular interface of inorganic salt ingredient and agrochemical ingredient under field application conditions permits an optimized enhancement of agrochemical efficacy. Less agrochemical ingredient can be utilized to achieve a prescribed degree of pest control or plant growth regulation. The alkaline pH provided by the hydrophilic inorganic salt ingredient facilitates the access of the agrochemical to the physiological systems of plants or pests.

The relative quantities of inorganic salt and agrochemical ingredients can be controlled with precision. Administration of one or more agrochemicals can be accomplished with ease and efficiency, and undesirable phytotoxic side effects can be minimized.

As a further advantage, two or more invention pulverulent compositions can be blended to provide formulations with precise quantities of two or more agrochemicals for polyfunctional activities in agricultural applications.

The following examples are further illustrative of the present invention. The components and specific ingredients are presented as being typical, and various modifications can be derived in view of the foregoing disclosure within the scope of the invention.

EXAMPLE I

This Example illustrates a process for the preparation of a pulverulent agrochemical composition in accordance with the present invention.

A.

$KHCO_3$ (10 g) is dissolved in 150 ml of water. Benomyl (50–150 microns, 100 g) is suspended in the aqueous solution with stirring.

The aqueous phase is removed by evaporation under vacuum. A dry free-flowing powder is obtained, in which the solid $KHCO_3$ is adsorbed as microcrystals on the surface of the Benomyl particles.

Both the KHCO$_3$ and Benomyl exhibit fungicidal activity in agricultural pest control applications, when utilized in diluted solid form, or as a suspension in an aqueous medium. The fungicidal efficacy of the Benomyl is enhanced by the presence of the KHCO$_3$ ingredient.

B.

Benomyl particles (100–250 microns, 2200 g) are coated by spraying with an aqueous medium of sodium lignosulfonate (35 g), and removing the water.

The coated Benomyl particles are placed in a rotating mix drum. $NaHCO_3$ (5–20 microns, 200 g) is uniformly distributed on the surfaces of the Benomyl particles employing the following electrostatic procedure.

The $NaHCO_3$ is loaded into an electrostatic powder spray gun by means of a gravity feed container. The $NaHCO_3$ is metered into a control console. The flow rate, fluidizing rate, atomizing rate and voltage level are set. The spray gun emits a fog-like cloud of charged $NaHCO_3$ particles into the mix drum in which the free falling Benomyl solids are being rotated. The mix drum unit is electrically grounded for safety.

EXAMPLE II

This Example illustrates the preparation of a fungicide dusting powder in accordance with the present invention.

The following ingredients are provided in the indicated proportions:

| | Parts |
|---|---|
| $NaHCO_3$ | 5 |
| $KHCO_3$ | 5 |
| triphenyltin acetate | 40 |
| talc | 500 |

Following the procedure of Example I, the $NaHCO_3$ and $KHCO_3$ are dissolved in 75 ml of water, and the triphenyltin acetate in particle form is suspended in the aqueous medium with stirring. The aqueous phase is removed by evaporation under vacuum.

The resultant dry powder is blended with the talc and milled to a dry pulverulent composition having a particle size less than 0.5 micron.

EXAMPLE III

This Example illustrates the preparation of a dinitroaniline-containing herbicide composition in the form of a wettable powder formulation.

The following ingredients are provided in the indicated proportions:

| | Parts |
|---|---|
| $NaHCO_3$ | 10 |
| $K_2CO_3$ | 5 |
| benfluralin (Balan) | 60 |
| sodium lignosulfonate | 2 |
| kaolin | 30 |

Following the procedure of Example I, the benfluralin in particle form is suspended in an aqueous solution of the $NaHCO_3$ and $K_2CO_3$ salts. The water is removed to provide a dry free-flowing powder in which microcrystals of inorganic salts are adsorbed on the surface of the benfluralin particles.

The prepared powder is blended with the sodium lignosulfonate and kaolin ingredients, and the blend is suspended in water to provide an aqueous formulation which contains about six pounds of benfluoralin per 500 gallons of water.

The aqueous formulation is applied in a quantity providing two pounds of benfluralin per acre of turf grass for the control of crabgrass.

EXAMPLE IV

This Example illustrates the preparation of an acylurea-containing agricultural insecticide composition in the form of a wettable powder formulation.

The following ingredients are provided in the indicated proportions:

| | Parts |
|---|---|
| $NaHCO_3$ | 10 |
| $K_2CO_3$ | 5 |
| diflubenzuron | 60 |
| sodium lignosulfonate | 2 |
| kaolin | 30 |

Following the procedure of Example I, the diflubenzuron in particle form is suspended in an aqueous solution of the $NaHCO_3$ and $K_2CO_3$ salts. After the water is removed, a dry free-flowing powder is recovered in which microcrystals of inorganic salts are adsorbed on the surface of the diflubenzuron particles.

The prepared powder is blended with the sodium lignosulfonate and kaolin ingredients, and the blend is dispersed in water (20% by weight solids) to form a stock medium. Aliquots of the aqueous formulation are diluted with water to 50, 100 and 500 ppm of diflubenzuron respectively, and tested for insecticidal activity.

The formulation is effective for 100 percent control of southern corn rootwood (*Diabrotica Undecimpunctate*) larvae and tobacco budworm (*Heliothis virescens*) larvae.

A synergistic insecticidal effect is noted for a formulation containing $NaHCO_3K_2CO_3$ in comparison with a formulation which does not contain $NaHCO_3/K_2CO_3$. Less diflubenzuron ingredient can be utilized for 100 percent control of larvae with a formulation containing $NaHCO_3/K_2CO_3$.

EXAMPLE V

This Example illustrates the preparation of fungicide composition tablets which rapidly disintegrate and disperse in water.

| | Parts |
|---|---|
| Captan | 40 |
| $NaHCO_3$ | 30 |
| citric acid | 12 |
| Lomar PWA 10[(1)] | 10 |
| polyethylene glycol (M.W. 4000) | 10 |
| sodium lignosulfonate | 2 |

[(1)]sodium salt of alkylarylsulfonate condensation product (Jacques Wolf & Co.)

[(1)] sodium salt of alkylarylsulfonate condensation product (Jacques Wolf & Co.)

Following the procedure of Example I, the Captan in particle form is suspended in an aqueous solution of the polyethylene glycol and 15 g of the $NaHCO_3$. The water is removed, and the resultant powder has a film of NaHCO₃/polyethylene glycol adsorbed on the surface of the Captan particles.

The prepared powder is blended with the citric acid, Lomar PWA 10 sodium lignosulfonate and the remainder of the NaHCO₃ (15 g) ingredient. The blend is formed into tablets which disintegrate and disperse in water within about six minutes at 25° C.

EXAMPLE VI

This Example illustrates the effectiveness of a preemergence herbicide in accordance with the present invention.

|  | Parts |
|---|---|
| hexazinone (Velpar) | 250 |
| NH₄HCO₃ | 100 |
| K₂CO₃ | 50 |
| sorbitol | 20 |
| ethoxylated sorbitan monolaurate | 30 |
| water | 150 |

Following the procedure of Example I, the hexazinone in particle form is suspended in an aqueous solution of the NH₄HCO₃, K₂CO₃ and sorbitol ingredients. The water is removed, and the resultant dry powder has a film of inorganic salts/sorbitol adsorbed on the surface of the hexazinone particles.

The prepared powder is blended with the ethoxylated sorbitan monolaurate ingredient, and the blend is suspended in water to form an aqueous emulsion.

The emulsion formulation is diluted with water to 250 ppm of herbicide ingredient. The diluted formulation is tested at the rate of 10 pounds per acre of herbicide ingredient, by drenching the formulation onto soil disposed in 4.5 inch plastic pots which contain respectively weed seeds of velvet leaf, jimsonweed, tall morningglory, switchgrass, barnyard grass, and green foxtail.

The percent control of each weed type is determined two weeks after treatment in comparison with untreated controls. The results indicate essentially 100 percent control of each weed type germination.

EXAMPLE VII

This Example illustrates the preparation of an acaricide-fertilizer composition for application to cultivated fields.

|  | Parts |
|---|---|
| malamine | 40 |
| urea | 30 |
| potassium glycerol phosphate | 20 |
| tetradifon | 15 |
| KHCO₃ | 5 |
| zeolite A | 80 |

Following the procedure of Example I, the tetradifon is suspended in an aqueous solution of the KHCO₃ salt ingredient. The water is removed, and a powder is obtained which has microcrystals of KHCO₃ adsorbed on the surface of the tetradifon particles.

The prepared powder is blended with the melamine, urea, potassium glycerol phosphate and zeolite A ingredients. Granules are prepared by tumbling the blend, spraying added water to form tacky solids, and then drying the granulated product.

What is claimed is:

1. A dry pulverulent composition which has a combination of ingredients comprising (1) a particulated fungicidal ingredient wherein the average particle size diameter is in the range between about 10–600 microns; (2) a fungicidal inorganic salt ingredient selected from the group consisting of alkali metal bicarbonates, ammonium bicarbonate and mixtures thereof, which is adsorbed on the surface of the particulated fungitidal ingredient; and (3) a compatibility enhancing ingredient selected from the group consisting of water-soluble organic . compounds which are in solid form at a temperature below about 10° C.

2. A composition in accordance with claim 1 wherein the compatibility enhancing ingredient is a monohydroxy or polyhydroxy compound, and the quantity of compatibility enhancing 3. A slow-release pulverulent composition which has a combination of ingredients comprising (1) a particulated fungicidal ingredient wherein the average particle size diameter is in the range between about 10–600 microns; (2) a blend ingredient comprising (a) a fungicidal inorganic salt ingredient selected from the group consisting of alkali metal bicarbonates, ammonium. bicarbonate and mixtures thereof, and (b) a water-soluble or water-dispersible organic polymer; wherein the blend ingredient is adsorbed on the surface of the particulated fungicidal ingredient, and the blend ingredient 4. A composition in accordance with claim 3 wherein the organic polymer in the blend ingredient is a polyhydroxy or polyoxyalkylene polymer.

5. A composition in accordance with claims 1 or 3 wherein the particulated fungicidal ingredient is benomyl.

* * * * *